(12) United States Patent
Park et al.

(10) Patent No.: US 8,753,636 B2
(45) Date of Patent: Jun. 17, 2014

(54) ACUTE LEUKEMIA AND LYMPHOBLASTIC LYMPHOMA-SPECIFIC CD43 EPITOPE AND USE THEREOF

(71) Applicant: Dinona Inc., Seoul (KR)

(72) Inventors: Seong-Hoe Park, Seoul (KR); Kyeong-Cheon Jung, Gangwon-do (KR); Eun-Young Choi, Seoul (KR); Seong-Pyo Park, Seoul (KR)

(73) Assignee: Dinona Inc., Seoul (KR)

( * ) Notice: Subject to any disclaimer, the term of this patent is extended or adjusted under 35 U.S.C. 154(b) by 0 days.

(21) Appl. No.: 13/842,942

(22) Filed: Mar. 15, 2013

(65) Prior Publication Data
US 2013/0287683 A1 Oct. 31, 2013

Related U.S. Application Data

(62) Division of application No. 12/577,115, filed on Oct. 9, 2009, now Pat. No. 8,426,555, which is a division of application No. 11/312,126, filed on Dec. 20, 2005, now Pat. No. 7,622,560.

(60) Provisional application No. 60/679,910, filed on May 11, 2005.

(30) Foreign Application Priority Data

Aug. 24, 2005 (KR) .............................. 2005-0077906

(51) Int. Cl.
*A61K 39/395* (2006.01)

(52) U.S. Cl.
USPC ..................................... 424/155.1; 424/141.1

(58) Field of Classification Search
None
See application file for complete search history.

(56) References Cited

PUBLICATIONS

Klco et al. (Int. Jnl. Lab. Hem. 2011, 33:555-565).*

* cited by examiner

*Primary Examiner* — Sharon Wen
(74) *Attorney, Agent, or Firm* — Alston & Bird LLP

(57) ABSTRACT

The present invention relates to a CD43 epitope expressed on human acute leukemia and lymphoblastic lymphoma cells and its use. More particularly, the present invention relates to a CD43 epitope expressed on human acute leukemia, lymphoblastic lymphoma cells, but not on mature hematopoietic cells, hematopoietic stem cells and non-hematopoietic cells, and to its diagnostic and therapeutic application on acute leukemia and lymphoblastic lymphoma.

6 Claims, 14 Drawing Sheets

ACUTE LEUKEMIA AND LYMPHOBLASTIC LYMPHOMA-SPECIFIC CD43 EPITOPE AND USE THEREOF

CROSS REFERENCE TO RELATED APPLICATION

This application is a divisional of U.S. Ser. No. 12/577,115 filed Oct. 9, 2009, which is a divisional of U.S. Ser. No. 11/312,126, filed Dec. 20, 2005, now issued as U.S. Pat. No. 7,622,560 on Nov. 24, 2009, which claims the benefit of U.S. 60/679,910 filed May 11, 2005 and Korean Patent Application No. 2005-0077906 filed Aug. 24, 2005, the entire content of each of which is incorporated herein by reference.

FIELD OF THE INVENTION

The present invention relates to a CD43 epitope expressed on human acute leukemia and lymphoblastic lymphoma cells and its use. More particularly, the present invention relates to a CD43 epitope exposed on human acute leukemia and lymphoblastic lymphoma cells, but not on mature hematopoietic cells and hematopoietic stem cells, and to its diagnostic and therapeutic application on acute leukemia and lymphoblastic lymphoma.

BACKGROUND OF THE INVENTION

The CD43 molecule, also called sialophorin or leukosialin, is a cell-surface molecules expressed on most of hematopoietic cells except erythrocytes. Human CD43 has a mucin-like extracellular domain of 235 amino acids (aa), a transmembrane domain of 23 as and a 123 as intracytoplasmic domain, all encoded by one exon (Pallant et al., Proc Nall Acad Sci USA. 1989, 86:1328-32; Shelley et al., Proc Natl Acad Sci USA 1989, 86:2819-23). The extracellular domain of human CD43 is rich the amino acids serine (46 residues) and threonine (47 residues), most of which carries about 80 0-linked carbohydrate chains. In addition, CD43 carries 1 N-linked carbohydrate chain. The structure of these O-glycans varies from one cell type to another (Carlsson et al., *J Biol. Chem.* 1986, 261:12787-95).

The CD43 gene consists of two exons, separated by a 378 by intron, whereby the entire translation product is encode by the second exon (Shelley et al., *Biochem J.* 1990, 270:569-76). CD43 has been believed to be a specific leukocyte-type marker restricted to most of leukocytes, platelets and hematopoietic stem cells, except for erythrocytes (Remold-O'Donnell et al., *Blood* 1987, 70:104-9; Fukuda, Glycobiology. 1991, 1:347-56). However, the expression of CD43 in human tumor cells of non-hematopoietic origin, such as a human uterine cervix cancer cell line (CaSKI), a human lung cancer cell line (A549), a human breast adenocarcinoma cell line (MCF7), a human fibrosarcoma cell line (HT 1080), and human colonic adenocarcinoma cell lines (COLO 205, HT 29, Caco-2, DLD-1 and SW480), has been demonstrated (Fernandez-Rodriguez et al., *Tumour Biol.* 2002, 23:193-201). CD43 is also expressed in human colon cancer tissue (Sikut et al, *Int J Cancer.* 1999, 82:52-8; Jung et al, *Korean J Pathol.* 38:8-14).

Biosynthetic studies show that the CD43 precursor, with a predicted size of around 40 kDa (including one N-glycan), migrates with an apparent molecular mass of 54 kDa upon electrophoresis. This precursor is subsequently converted to a mature glycosylated molecule with sized from 115 kDa to up to more than 200 kDa due to variable glycosylation. Thymocytes, CD4+ T lymphocytes and monocytes express more of a 115 kDa isoform, whereas a 130 kDa form is found mostly on activated CD4+ T cells, CD8' resting and activated T cells, neutrophils, platelets and B cells (Rosenstein et al., *Immunol Res.* 1999, 20:89-99). It seems that more than one isoform can be co-expressed on the surface of the same cc 11. A tightly regulated post-translational 0 glycosylation pattern results in these characteristic molecular weight isoforms that are differentially expressed in different cell types. Especially, expression of core 2 p-1,6-N-acetylglucosaminyltransferase (C2GnT) results in expression of the 130 kDa CD43 isoform in thymocytes and T cells (Piller et al., J Biol. Chem. 1988, 263:15146-50).

Until recently, more than 17 anti-human CD43 antibodies had been reported. Most of these antibodies react with carbohydrate epitopes on the extracellular domain and all known anti-CD43 antibodies detect the CD43 protein expressed on mature hematopoietic cells (Table 1). Thus, they are not efficient at detecting or eradicating leukemic or lymphoma cells.

TABLE 1

| Anti-CD4 antibody | CD43-positive cells | CD43-negative cells | Epitope | *Reference |
|---|---|---|---|---|
| T305 | Activated CD4+ cells, CD8+ T cells, thymocytes, myeloid precursors in bone marrow | Granulocytes, erythrocytes, platelets carbohydrate | Core-2 | 1, 2 |
| L10 | T cells, thymocytes, B cell lines, monocytes, neutrophils, platelets | Erythrocytes | 1-78 Sialidase-resistant 178 | 3 |
| L2 | T cells, thymocytes, B cell lines, monocytes, neutrophils, platelets | Erythrocytes | | |
| 84-3C1 | Bone marrow cells, thymocytes, T cells, monocytes, granulocytes | Platelets, erythrocytes | Sialidase-sensitive carbohydrate | 4 |
| MEM-59 | Most of leukocytes, CD34+ bone marrow cells | | Neuraminidase-sensitive carbohydrate | 5, 6 |
| MT-1, L60 | T cells, monocytes | B cells | Neuraminidase-sensitive carbohydrate | 7 |
| DFT1 | T cells, monocytes | B cells | | |

TABLE 1-continued

| Anti-CD4 antibody | CD43-positive cells | CD43-negative cells | Epitope | *Reference |
|---|---|---|---|---|
| 1G10 | T cells, NK cells, granulocytes | B cells, Erythrocytes | | 8 |
| CBF.78 | T cells, subsets of monocytes and granulocytes | | Neuraminidase-resistant | 9 |
| RDF/AD-9 | T cells, monocytes, granulocytes | B cells | Neuraminidase-sensitive carbohydrate | |
| 161-46 | T cells, monocytes, granulocytes | B cells | Neuraminidase-resistant | |
| 4D2 | COLO 205, K562, Jurkat | | Intracellular (337-343 | 10 |
| 4D1 | Activated CD4+ T cells, monocytes | B cells | Core-2 carbohydrate | Mukasa et al., 1999 |

*1. Fox et al., *J Immunol.* 1983, 131: 762-7; 2. Saitoh et al., *Blood.* 1991, 77: 1491-9; 3. Remold-O'Donnell et al., *Blood.* 1987, 70: 104-9; 4. Borche et al., *Eur JImmunol.* 1987, 17: 1523-6; 5. Stefanova et al., *Folia Biol (Praha).* 1988, 34: 255-65; 6. Alvarado et al., *Eur J Immunol.* 1995, 25: 1051-5; 7. Stross et al, *J Clin Pathol.* 1989, 42: 953-61; 8. Horejsi et al., 1997, *In Kishimoto T, et al, Leucocyte Typing, Vol. VI: White Cell Differentiation Antigens 494.* Garland, New York and London; 9. Tkaczuk et al., *Tissue Antigens.* 1999, 54: 1-15; 10. Sikut et al., *Int J Cancer.* 1999, 82: 52-8; 11. Mukasa et al, *Int Immunol.* 1999, 11: 259-68.

SUMMARY OF THE INVENTION

An object of the present invention is to provide an acute leukemia, chronic leukemia with blast crisis and lymphoblastic lymphoma-associated CD43 epitope where the epitope is exposed on human acute leukemia and lymphoblastic lymphoma cells, but not on mature hematopoietic cells and hematopoietic stem cells. Thus, the present invention provides an isolated polypeptide for epitope of CD43 comprising an amino acid sequence of SEQ ID NO: 1.

Another object of the present invention is to provide material that recognizes the CD43 epitope. Preferably, the present invention provides an antibody or its fragment which specifically binds to an epitope of CD43 comprising an amino acid sequence of SEQ ID NO: 1.

A third object of the present invention is to provide a method for producing the materials that recognize the CD43 epitope.

A fourth object of the present invention is to provide material for the diagnosis of acute leukemia, chronic leukemia with blast crisis, and lymphoblastic lymphoma.

A fifth object of the present invention is to provide a method of diagnosing acute leukemia, chronic leukemia with blast crisis, and lymphoblastic lymphoma. Thus, the present invention provides a method of diagnosing acute leukemia comprising leukemia cells in a biological sample with anti-CD43 epitope antibody, and detecting the positive reaction to the anti-CD43 epitope antibody. The present invention provides a method of diagnosing chronic leukemia with blast crisis comprising incubating leukemia cells in a biological sample with anti-CD43epitope antibody, and detecting the positive reaction to the anti-CD43 epitope antibody. The present invention provides a method of diagnosing lymphoblastic lymphoma comprising incubating lymphoma cells in a biological sample with anti-CD43 epitope antibody according to claim 6, and detecting the positive reaction to the anti-CD43 epitope antibody.

A sixth object of the present invention is to provide a pharmaceutical composition which can kill tumor cells of acute leukemia, chronic leukemia with blast crisis and lymphoblastic lymphoma.

A seventh object of the present invention is to provide a method for diagnosis by use of the diagnostic material of the present invention. In addition, the present invention is to provide a method for treatment by use of the therapeutic material of the present invention.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein.

DETAILED DESCRIPTION OF THE EMBODIMENTS

Figure 1:
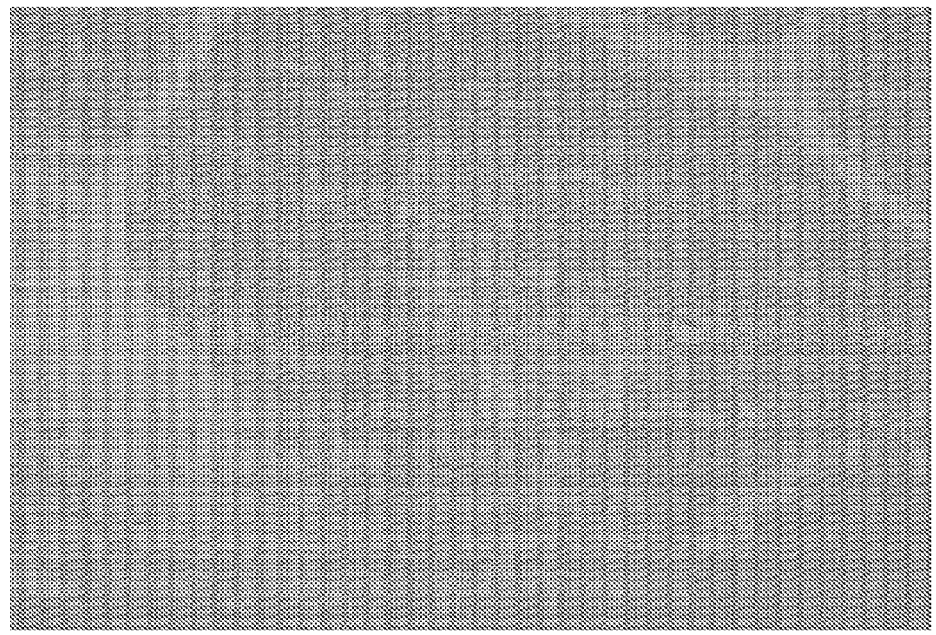
FIG. 1 is a photograph of immunohistochemical staining of thymus by supernatant of hybridoma clone producing EB-1 monoclonal antibody specific against the CD43 epitope. The hybridoma has been deposited subject to the Budapest Treaty as accession number KCLRF-BP-00010 at the Korean Cell Line Research Foundation, Cancer Research Institute, Seoul National Univ. College of Medicine, 28 Yungon-dong, Chongno-gu, Seoul, 110-799, Korea on Jan. 14, 1997.

The present invention is to provide a CD43 epitope exposed on the tumor cells of acute leukemia, chronic leukemia with blast crisis and lymphoblastic lymphoma, but not on mature hematopoietic cells and hematopoietic stem cells. The CD43 of the present invention is a preferably human CD43, which sequence had been submitted to the NCBI GenBank under accession No. M61827. The CD43 epitope is any polypeptide that includes amino acid sequence in SEQ ID NO: 1 (hereinafter, EP6), and more preferably includes amino acid sequence in SEQ 1:D NO: 2 (hereinafter, EP9).

```
EP6:
                                            (SEQ ID NO: 1)
Pro Leu Tip Thr Ser Ile

EP9:
                                            (SEQ ID NO: 2)
Glu Gly Ser Pro Leu Trp Thr Ser Ile.
```

In a preferred embodiment, the present invention provides a polypeptide of less than 200 amino acids in length, more preferably less than 100 amino acids in length, more preferably less than 50 amino acids in length, comprising an amino acid sequence of SEQ ID NO:1 or SEQ ID NO:2.

The present invention also provides a polypeptide consisting essentially of an amino acid sequence of SEQ ID NO:1 or SEQ ID NO:2. The present invention also provides a polypeptide consisting of an amino acid sequence of SEQ ID NO:1 or SEQ ID NO:2.

The CD43 epitope (EP6 and EP9) could be purified from human tissues, chemically synthesized, or produced by biotechnology.

Also, the present invention is to provide material recognizing the CD43 epitope of the present invention. The material is selected from the group consisting of antibody, its fragment, and ligands, and the antibody is preferably selected from the group consisting of monoclonal and polyclonal antibody, and more preferably it is originated from human and animal.

The antibodies comprise parts of antibody including antigen recognition region ($V_H$ and $V_L$), so has the capacity to recognize antigen preferentially. In addition, it also includes antibody fragment, such as F(ab')2, Fab and Fv. Preferentially the antibody fragment (Fv) comprises a single chain polypeptide fragment of antibody, so called single chain Fv, which is prepared by inserting a linking peptide between two polypeptides, $V_H$ and $V_L$ to increase heat stability.

The present invention further provides chimeric antibodies recognizing the CD43 epitope of the present invention. As used herein, the term "chimeric antibody" refers to an antibody in which the variable regions of antibodies derived from one species are combined with the constant regions of antibodies derived from a different species or alternatively refers to CDR grafted antibodies. Chimeric antibodies are constructed by recombinant DNA technology, and are described in Shaw, et al., J. Immun., 138:4534 (1987), Sun, L K., et al., Proc. Natl. Acad. Sci. USA, 84:214-218 (1987), for example.

Other known techniques can be used to generate CDR grafted and chimeric antibodies. "CDR" or "complementarity determining region" or "hypervariable region" is defined as the amino acid sequences on the light and heavy chains of an antibody which form the three-dimensional loop structure that contributes to the formation of the antigen binding site.

As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

The terms "light chain variable region" and "heavy chain variable region" refer to the regions or domains at the N-terminal portion of the light and heavy chains respectively which have a varied primary amino acid sequence for each antibody. The variable region of the antibody consists of the amino terminal domain of the light and heavy chains as they fold together to form a three-dimensional binding site for an antibody.

The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., Antibody Engineering: A Practical Guide, W.H. Freeman and Company, New York, 1992, incorporated by reference).

This invention further provides humanized antibodies recognizing the CD43 epitope of the present invention. As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. See e.g., Cabilly U.S. Pat. No. 4,816,567; Queen et al. (1989) Proc. Nat'l Acad. Sci. USA 86:10029-10033; and ANTIBODY ENGINEERING: A PRACTICAL APPROACH (Oxford University Press 1996).

In one preferred embodiment of the present invention, the antibody binds to a peptide consisting of the amino acid sequence shown in SEQ ID NO:1.

The antibody or its fragment may further comprise labeling material which is selected from the group of radioisotopes, toxins, fluorescent materials and staining materials. The examples of the fluorescent materials are fluorescein-5-isothiocyanate (FITC), phycoerythrin(PE), allophycocyanin (APC), and biotin, but does not limited thereto.

The antibody or its fragment may further comprise a toxic material selected from the group consisting of radioisotopes, toxic chemicals, toxic proteins and anti-tumor agents. The antibody or its fragment is combined with the toxic proteins to produce a fusion protein. The examples of the toxic proteins include ricin, saporion, gelonin, momordin, diphtheria toxoid and pseudomonas toxin, but does not limited thereto.

The present invention also provides a method for producing the material, and it provides cells producing the antibody. The method of producing antibody or its fragment includes the steps of (a) immunizing an animal with polypeptide, protein or protein fragments containing or cells expressing the CD43 epitope, (b) extracting splenocytes from the immunized animal, (c) fusing the splenocytes with myeloma cells, and (d) screening hybridoma cells producing antibodies against the CD43 epitope. The material can be obtained by in vitro culture or injection into the animals of cells producing the materials. The material can be obtained from the ascites of animals in which the cells producing the materials are intraperitoneally injected. The materials can be purified from the culture supernatant or ascites by ion exchange chromatography or affinity column chromatography.

In an embodiment, the present invention relates to a pharmaceutical composition for treating the acute leukemia, the chronic leukemia with blast crisis, lymphoblastic lymphoma comprising an anti-CD43 epitope antibody or its fragment, and a pharmaceutically acceptable carrier.

Administration of the antibody or its fragment according to the invention can be carried out using any of the accepted modes of administration of pharmaceutical compositions. Thus, administration can be, for example, The antigen recognition material can be administered orally or 10 more preferably parenterally into the patients, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and the antibody of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The suitable dosage of the active component can be selected depending on the condition of the subject, for example 3 mg to 6,000 mg per 1 day.

In an embodiment, the present invention relates to a method of treating the acute leukemia, the chronic leukemia with blast crisis, lymphoblastic lymphoma using the antibody or its fragment, which is selected from the group consisting of antibody, antibody fragment, single chain polypeptide antibody fragment and ligand. The antibody or the antibody fragment is preferably selected from the group consisting of monoclonal and polyclonal antibodies, and more preferably it is originated from human and animal. Preferably the antibody or its fragment further includes toxic material which is selected from the group consisting of radioisotopes, toxic chemicals, toxic proteins and anti-tumor agents.

Further, the present invention provides a method for the diagnosis of acute leukemia, chronic leukemia with blast crisis and lymphoblastic lymphoma using the antibody or its fragment. The method includes the steps of (a) incubating the antibody or its fragment with a cell in a biological sample, and (b) detecting the sample showing positive reaction against the antibody. The tumor is preferably acute leukemia, chronic leukemia with blast crisis or lymphoblastic lymphoma.

In addition, the present invention provides a diagnostic kit for acute leukemia, chronic leukemia with blast crisis and lymphoblastic lymphoma using the material. The diagnostic kit could include the method for the detection of antigen-antibody reaction in addition to the material. The detection method is preferably selected from the group consisting of flow cytometry, immunohistochemistry, enzyme-linked immunosorbent assay (ELISA), radioimmunoassay (MA), enzyme immunoassay (EIA), fluorescence immunoassay (FIA) and luminescence immunoassay (LIA). The detection method include the labeling materials, which could be selected from the group of enzymes (such as horse radish peroxidase (HRP)), fluorescent materials (such as FITC), luminescent materials (such as luminol, isoluminol and lucigenin), and isotopes (such as $^{125}I$, $^{3}H$, $^{14}C$ and $^{131}I$), but is not to be considered limiting thereof in any way. The reactivity of the antigen recognition material could be confirmed using device detecting the enzyme reaction, fluorescence, luminescence, or radiation. The diagnosis kit can be made in flow cytometry kit, immunohistochemistry kit, ELISA kit or strip kit including the antibody or its fragment.

The present invention is further explained in more detail with reference to the following examples. These examples, however, should not be interpreted as limiting the scope of the present invention in any manner.

EXAMPLE 1

In order to discover a specific cell surface protein on thymocytes, human thymocytes were administrated into Balb/c mice to produce antibodies to human thymocytes by the following examples.

$10^7$ of human thymocytes were intraperitoneally administrated and immunized into Balb/c mice at two weeks interval for six weeks. The spleen of Balb/c mice was removed 3 days after last administration to prepare the spleen cell suspension. Monoclonal antibodies were produced by fusing the spleen cells of Balb/c immunized with human thymocytes with SP2/0-Ag14 mouse myeloma cells resistant to 9-azaguanine. Cell fusion method followed Koeler and Milstein method (Koeler & Milstein *Nature*, 1975, 256, 495-497). $10^8$ spleen cells were fused with $10^7$ myeloma cells using 50% polyethylene glycol 4000. The cells were washed and resuspended in Dulbeco's modified Eagle's medium (DMEM) containing 20% bovine serum albumin, 100 μM hypoxanthine, 0.44 μM aminopterin and 16 μM thymidine (HAT media). The cells were introduced to four 96-well plates and cultured at 37☐, and 5% $CO_2$ incubator. When colonies were formed after two weeks, the supernatant was prepared and the reactivity of antibody was observed using immunohistochemistry and flow cytometry.

The well containing more than $10^5$ cells per well was regarded as positive group. Cells were taken from the well containing highly reactive antibody, and subcloned 0.5 cell per well by limiting dilution assay to produce stable hybridoma clone with high reactivity of antibody. This hybridoma clone secretes antibody into the media and the supernatant was stored for the next steps.

EXAMPLE 2

In order to discover a clone which secrets antibody recognizing the specific cell surface antigen on thymocytes among the hybridoma clones produced by Example 1, the immunoperoxidase staining was carried out on the slide of 4 um thick of fresh tissue and formalin-fixed paraffin-embedded tissue using the supernatant of the hybridoma clone produced by Example 1 according to avidin-biotin complex (ABC) staining method by binding avidin with biotin. The supernatant of monoclonal cell was used as primary antibody. The paraffin embedded tissue was treated with normal mouse serum and allowed to stand for 1 hour to prevent nonspecific background staining after removal of paraffin. After adding a primary antibody, they were allowed to stand overnight and washed three times with phosphate buffered saline (PBS). Biotinylated goat anti mouse immunoglobulin used as a secondary antibody was added. It was allowed to stand at room temperature for 1 hour, washed three times with PBS. Then streptavidine and horse-radish peroxidase conjugate was added. 3,3'-diaminobezidine tetrahydrochloride (DAB) and $H_2O_2$ solution manufactured by DAKO was added to stain cells, treated for 20 minutes and washed three times with PBS. It was observed under light microscopy after covering with cover glass.

Hybridoma clone lines producing antibody specific for human thymocytes were selected. One of clones whose antibody recognized thymocytes was named as EB-1. FIG. 1 is a photograph of immunohistochemical staining thymus with the supernatant of hybridoma clone producing EB-1 antibody. As shown in FIG. 1, most of thymocytes is positively stained. Cell surface of thymocytes were strongly stained so the antigen recognized by EB-1 antibody is cell surface antigen.

EXAMPLE 3

Figure 2:
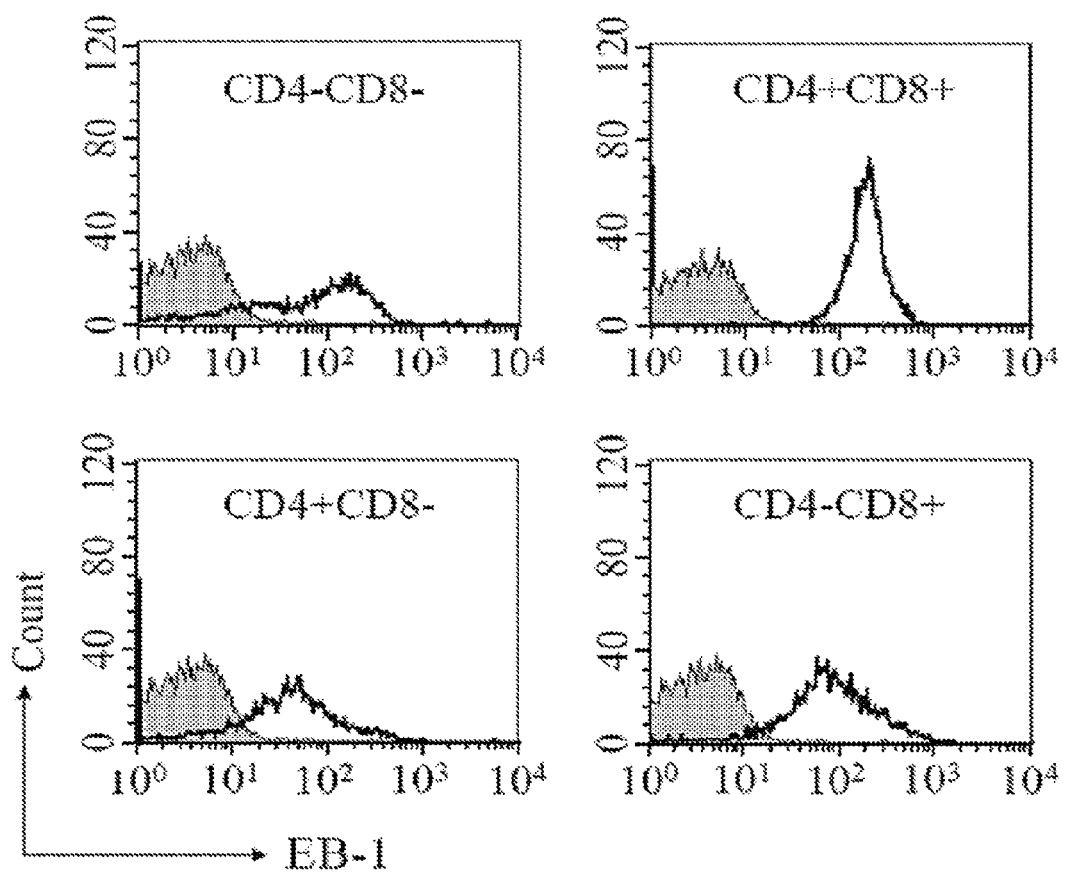
FIG. 2 is a photograph of the reactivity of EB-1 monoclonal antibody on the surface of human thymocytes using triple color flow cytometry.

To evaluate the reactivity of EB-1 antibody according the developmental stages of thymocytes, flow cytometry was carried out. Human thymuses, which were removed from patient during cardiac surgery, were finely teased, and single cell suspension was prepared, $1 \times 10^6$ cells were suspended in 100 μl PBS, and distributed into test tubes. 100 μl EB-1 culture supernatant was added and stirred. The solution was reacted at 4° C. for 30 minutes, centrifuged at 1,500 rpm for 5 minutes, and the pellet was washed twice with PBS to remove the unreacted antibody. The pellet was suspended in 50 μl solution containing diluted secondary antibody (FITC-conjugated goat anti-30 mouse Ig manufactured by Zymed, reacted at 4° for 30 minutes in a dark room. After washing twice, the pellet was suspended in 50 μl solution containing phycoerythrin (PE)-conjugated anti-CD8 antibody and allophycocyanin (APC)-conjugated anti-CD4 antibody, reacted at 4° for 30 minutes in a dark room, and then washed twice. Finally 200 μl of PBS was added to the cell pellet after centrifugation. Thymocytes are classified into four subsets according to the expression pattern of CD4 and CD8 (that is, CD4 CD8 double negative thymocytes, $CD4^+CD8^+$ double positive thymocyte, and $CD4^+CD8$ or $CD4CD8^+$ single positive thymocytes) and the ratio of EB-1-positive cells and the intensity and EB-1-staining were analyzed by flow cytometry. FIG. 2 shows the results of three color flow cytometric analyzing showing the reactivity of EB-1 against all subsets of thymocytes, particularly the highest staining intensity on double positive thymocytes. In FIG. 2, the solid line represents the staining by EB-1 antibody, and the negative staining profile by an irrelevant antibody is shown as filled histogram.

EXAMPLE 4

In order to obtain high concentration of antibody secreted by EB-1-screting hybridoma clone, ascites were prepared. Three weeks after 0.5 ml of pristine was administrated intraperitoneally into Balb/c mouse, $10^7$ of EB-1 hybridoma clone cultured in DMEM containing 10% bovine serum. After 2 to 3 weeks, ascites were collected. Then the concentration of antibody was 5 to 10 mg/ml. Only immunoglobulins responding to human thymocytes were purified because there are many contaminating proteins such as albumin in ascites. To purify antibody from ascites containing high amount of antibodies obtained from Balb/c mouse into which EB-1 monoclonal hybridoma cells were intraperitoneally administered, Q-Sepharose chromatography and hydroxyapatite (Bio-gel HTP Gel manufactured by Pharmacia) chromatography were performed.

3.14 g of ammonium sulfate per 10 ml of ascites was slowly added on ice (precipitated with 50% of $(NH4)2 SO4$). The mixture was centrifuged at 15,000 rpm for 30 minutes, resuspended in deionized water and dialyzed in 1 liter of buffer solution (20 mM phosphate, pH 7.4). The solution was passed and absorbed in Q-Sepharose column previously equilibrated with buffer solution (20 mM phosphate, pH 7.4), and then the buffer solution was again passed through the column to remove free proteins in the column, after which the protein absorbed in column was eluted with linear gradient 0 M to 0.8 M of NaCl using buffer solution I (20 mM phosphate, pH 7.4) and buffer solution II (20 mM phosphate and 8.5 M NaCl, pH 7.4). Each fraction was electrophoresized in SDA-PAGE and the fractions containing EB-1 antibody were collected.

The fractions were then dialyzed in buffer solution (20 mM phosphate, pH 6.8), and put through hydroxyapatite column previously equilibrated with buffer solution (20 mM phosphate, pH 6.8). The fraction in buffer solution (20 mM phosphate, pH 6.8) passed through the column to remove free proteins and was eluted with a linear gradient 0 to 0.3 M of phosphate using buffer solution III (20 mM phosphate, pH 6.8) and buffer solution (300 mM phosphate, pH 6.8). Each fraction was electrophoresized in SDS-PAGE and the fractions containing more than 95% of EB-1 antibody were collected. EB-1 antibody collected was dialyzed in appropriate buffer solution and stored. 5 to 10 mg EB-1 antibody was prepared from 1 ml of ascites by repeated experiments.

EXAMPLE 5

The present example was carried out according to flow cytometric analysis of Example 3 to investigate whether EB-1 antibody is reactive against normal leukocytes except thymus using EB-1 antibody purified from Example 4 as primary antibody. For this analysis, the purified EB-1 antibody was directly combined with FITC or PE, in which case it was not necessary to use the secondary antibody for fluorescence, or biotin-conjugated EB-1 antibody was used combined with fluorescent-conjugated streptavidine.

Figure 3:
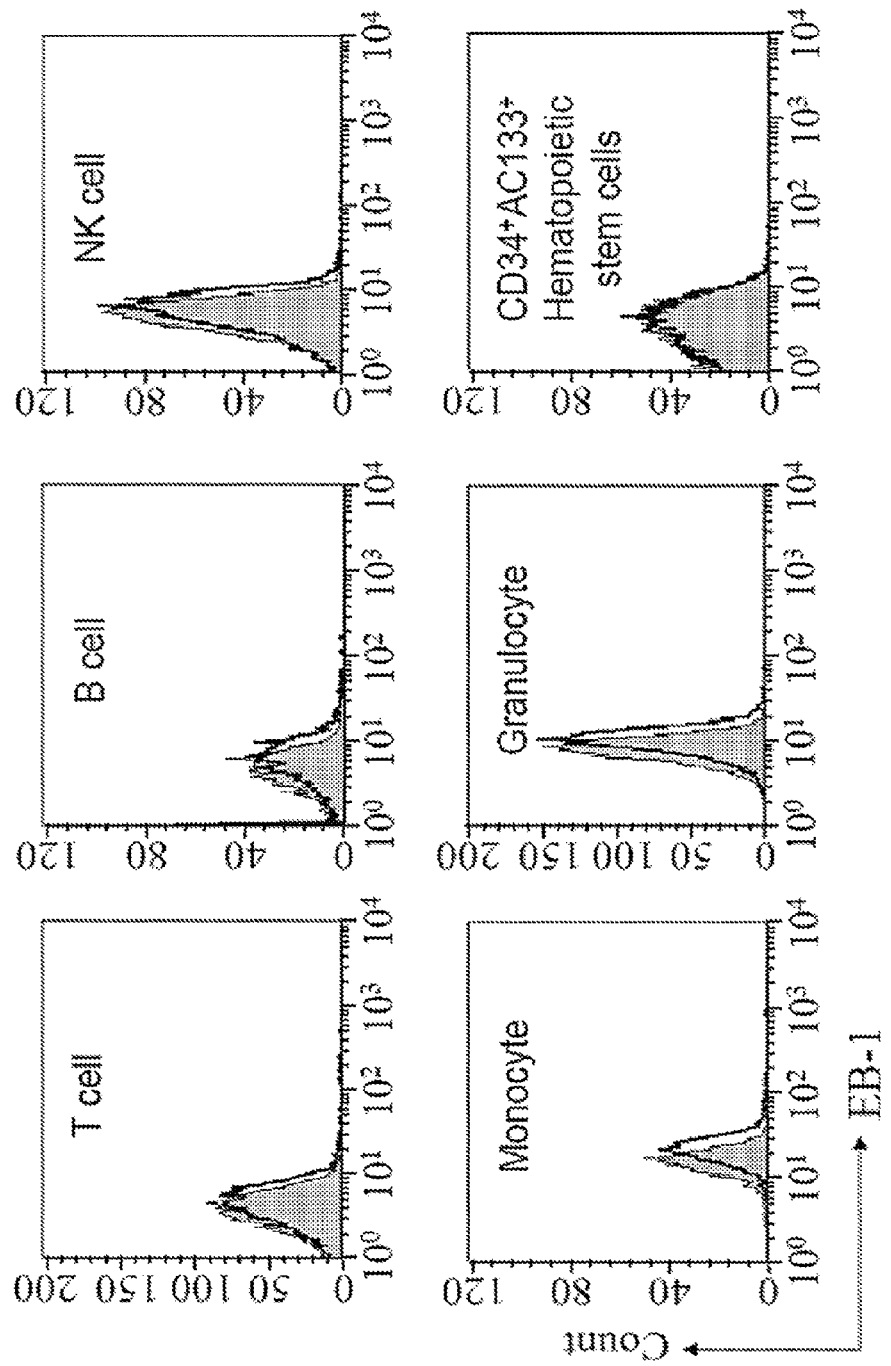
FIG. 3 is a photograph of the reactivity of EB-1 monoclonal antibody on the surface of human peripheral blood leukocytes and hematopoietic stem cells of cord blood using triple color flow cytometry.

Table 2 below shows the reactivity of EB-1 antibody on the cell surface of normal peripheral blood leukocytes, activated peripheral blood mononuclear cells cultured in the medium containing 10 μg/ml of Phytohemagglutinine (PHA) or 5 pig/ml of anti-CD3 antibody, normal spleen cell, normal thymocytes, and $CD34^+AC\ 133^+$ hematopoietic stem cells in cord blood. All of them were negative to EB-1 antibody, except for thymocytes. The representative results of flow cytometric analysis of normal leukocytes are shown in FIG. 3, in which the solid line represents the staining by EB-1 antibody, and the negative staining profile by an irrelevant antibody is shown as filled histogram.

TABLE 2

| Cells | EB-1-Positivity |
| --- | --- |
| Peripheral blood cells | |
| Erythrocytes | −* |
| Lymphocytes | − |
| Monocytes | − |
| Granulocytes | − |
| Platelets | − |
| Activated peripheral blood | |
| PHA (10 µg/ml) | − |
| Anti-CD3 antibody (5 µg/ml) | − |
| Splenocytes | − |
| Thymocytes | ++* |
| CD34$^+$AC 133$^+$ hematopoietic stem cells in cord blood | − |

*Negative staining
**Positive staining in more than 90% of cells
PHA, Phytohemagglutinine

EXAMPLE 6

The present example was carried out according to immunohistochemical assay of Example 2 to confirm whether EB-1 antibody is reactive against normal tissue except thymus using EB-1 antibody purified from Example 4 as primary antibody. Table 3 below is the reactivity of EB-1 antibody in each of the various tissues. Except for thymocytes, all other tissues including peripheral lymphoid tissue, cerebellum, pancreas, ovary and testis, skin, lung, adrenal, and kidney were negative for staining.

TABLE 3

| Organ | No. of cases | No. of EB-1 positive |
| --- | --- | --- |
| Lymphoid System | | |
| Lymph node | 18 | 0 |
| Tonsil | 3 | 0 |
| Thymus | 6 | 6 |
| Spleen | 4 | 0 |
| Nervous System | | |
| Cerebrum | 4 | 0 |
| Cerebellum | 4 | 0 |
| Digestive System | | |
| Esophagus | 3 | 0 |
| Stomach | 10 | 0 |
| Small intestine | 2 | 0 |
| Large intestine | 2 | 0 |
| Liver | 7 | 0 |
| Pancreas | 4 | 0 |
| Vermiform appendix | 4 | 0 |
| Reproductive System | | |
| Testis | 2 | 0 |
| Ovary | 8 | 0 |
| Uterus | 4 | 0 |
| The Others | | |
| Lung | 8 | 0 |
| Kidney | 9 | 0 |
| Adrenal gland | 5 | 0 |
| Skin | 4 | 0 |

EXAMPLE 7

Figure 4:
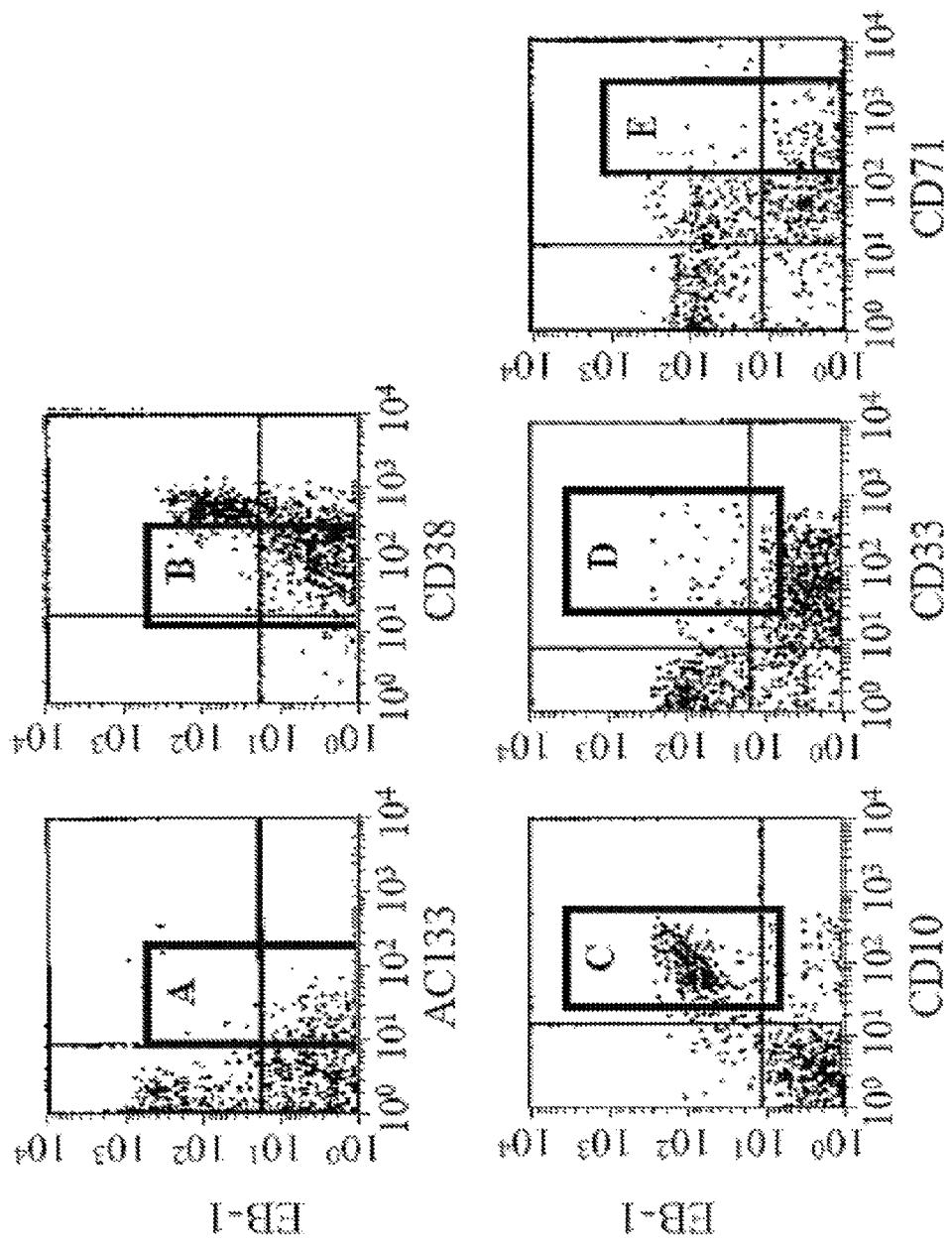
FIG. 4 is a photograph of the reactivity of EB-1 monoclonal antibody on the surface of human bone marrow cells using triple color flow cytometry.

The present example was carried out according to flow cytometric analysis of Example 3 to whether EB-1 antibody is reactive against normal bone marrow cells using EB-1 antibody purified from Example 4 as primary antibody. For this analysis, biotin-conjugated EB-1 antibody and APC-conjugated streptavidine was used in combination with FITC-conjugated anti-CD10, anti-CD33, anti-CD38, anti-CD71, or anti-AC133, and PE-conjugated-anti-CD34. FIG. 4 is the result of three color flow cytometric analysis, in which CD34$^+$ cells were gated. Pluripotent stem cells were defined as CD34$^+$AC133$^+$ (FIG. 4A) or CD34$^+$CD38$^{-/dim}$ (FIG. 4B) cells in bone marrow or cord blood and they did not show reactivity against EB-1 antibody at all. In addition, CD34$^+$CD33$^+$ cells (FIG. 4D) that contain virtually all the colony-forming cells such as progenitor cells capable of forming granulocytes, erythrocytes, monocytes, megakaryocytes (CFU-GEMM), CFU-GM, and burst-forming unit erythrocytes, and CD34$^+$CD71$^{bright}$ erythroid-committed progenitor cells (FIG. 4E) were also not stained by EB-1 antibody. In contrast, positive staining of EB-1 antibody was observed on the majority of lymphoid-committed CD34$^+$CD10$^+$ precursors (FIG. 4C).

In summary of the results, EB-1-reativity was restricted to thymocytes and some hematopoietic precursors in bone marrow, but not found in any another hematopoietic cells including mature peripheral blood cells and hematopoietic stem cells and non-hematopoietic tissues.

EXAMPLE 8

In order to clarify the antigen recognized by EB-1 antibody, a cDNA library of human thymocytes was prepared using poly(A)+ RNA and the pcDNA3 expression vector manufactured by Invitrogen. This library contained 3.5×106 independent colonies. The strain of bacterial host used was *Escherichia coli* MC1061/P3. Plasmid pMIK/D3T 31 was constructed by inserting XhoI fragment of Gb3 synthase cDNA clone, pD3T 31 (Haraguchi et al., Proc. Natl. Acad. Sci. U S. A. 1994, 91: 10455-9), into pMIK/Neo expression vector.

Plasmids of the cDNA library were once amplified and transfected into 293T cells together with plasmid pMIK/D3T-31 using DEAE-dextran as described previously (Davis et al., Methods in Molecular Biology, Elsevier Science, New York 1986:285-289). Subconfluent 293T cells, 1.5×10$^6$ in 10-cm dishes were co-transfected with 8 µg each of cDNA library plasmid and pMIK/D3T-31. After 60 h, the transfected cells were detached from plates and incubated with EB-1 antibody at a 1:200 dilution on ice for 45 minutes. Cells were plated on dishes coated with goat anti mouse IgM as described previously (Wysocki et al., Proc. Natl. Acad. Sci. U.S.A. 1978, 75:2844-8). Plasmid DNA was rescued from the panned cells and transformed into 293T. Expanded plasmid DNA was transfected again, and the same procedure was repeated four times more. Thereafter 96 pools containing 30 colonies each were prepared and screened by EB-1 reactivity. Finally, 17 clones from two positive pools were screened, and three single colonies that directed the EB-1 reactivity on 293T were isolated using microscale DEAE-dextran transfection and immunofluorescence assay.

Isolated cDNA plasmid was digested by XhoI and HinIII and cloned into phagemid BlueScript (pBSK) KS(+) vector. Deletion mutants of this clone were prepared with a Kilo-Sequence deletion kit. Dideoxynucleotide termination sequencing was performed by either T3/T7 dye primers or four additional custom dideoxy terminators with the PRISM™ dye terminator cycle sequencing kit and model 377 DNA sequencer manufactured by Applied Biosystems. Blast search using the DNA sequence identified through this procedure revealed that the antigen recognized by EB-1 antibody is human CD43.

Figure 5:
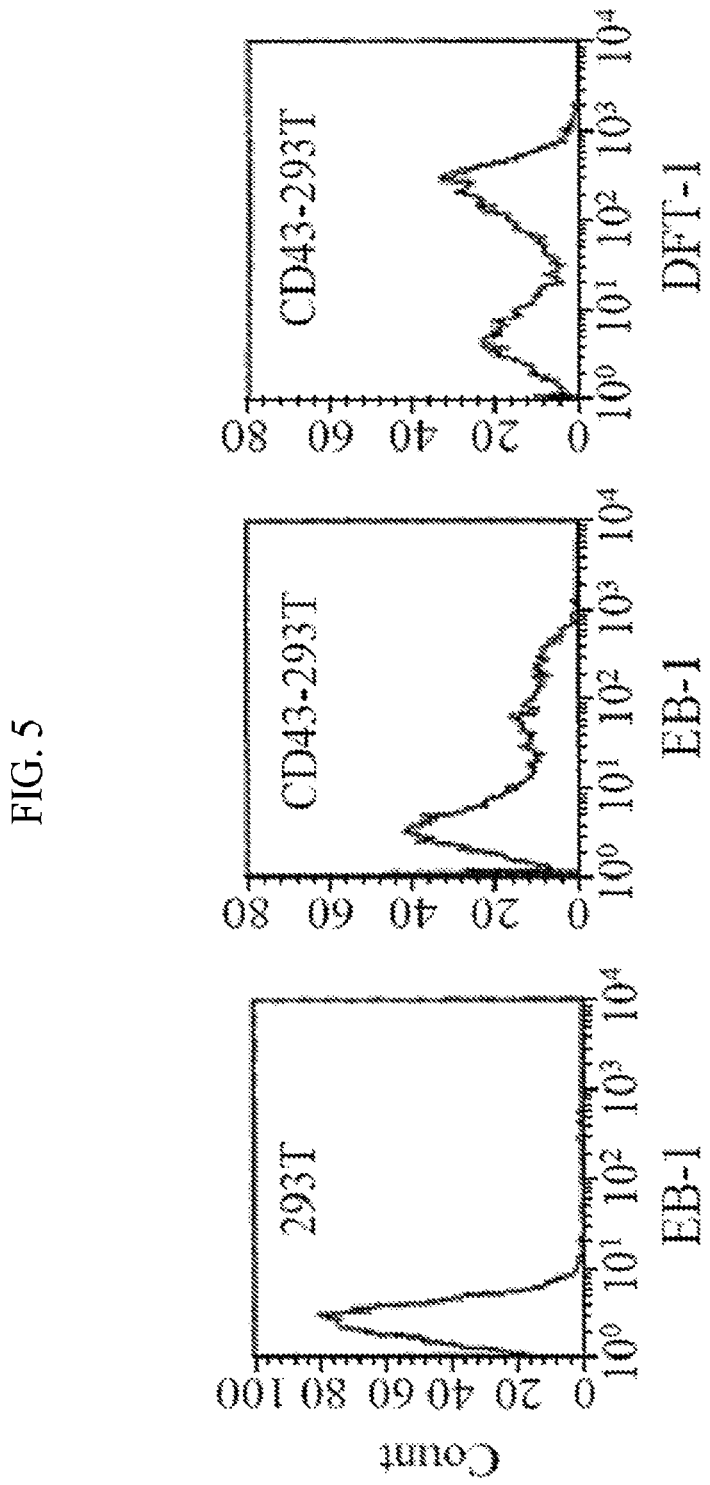
FIG. 5 is a photograph of the reactivity of EB-1 monoclonal antibody on the surface of human CD43-transfected 293T cell line using single color flow cytometry.

To confirm that the EB-1 antibody recognized human CD43 antigens, human CD43 transfected 293T cells were stained with EB-1 antibody and a well known anti-CD43 antibody, DFT-1. As shown in FIG. 5, EB-1 antibody was not reactive against wild-type 293T cells, whereas CD43 transfected 293T cells were stained by both EB-1 and DFT 1 antibodies. Thus, EB-1 is a monoclonal antibody against human CD43.

Figure 6:
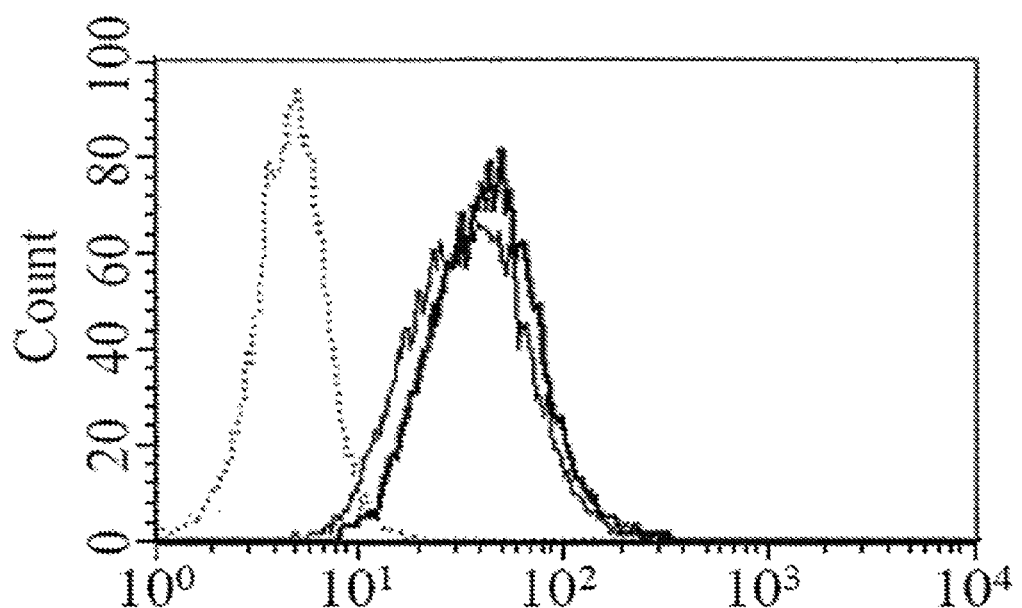
FIG. 6 is a photograph of the reactivity of EB-1 monoclonal antibody on the surface of human Molt-4 cell line with or without sialidase treatment using single color flow cytometry.

As CD43 is heavily glycosylated protein, we investigated whether sialidase treatment of CD43 molecules modify the immunoreactivity of EB-1 antibody against CD43 antigen. FIG. 6 shows a flow cytometric analysis of Molt-4 cells with or without sialidase treatment. The dotted line represents the negative staining profile by an irrelevant antibody, and thin and thick solid lines represent the immunoreactivity of EB-1 antibody on the sialidase-untreated and treated Molt-4 cells, respectively. The immunoreactivity of EB-1 antibody on Molt-4 cells was not affected by sialidase treatment.

Figure 7:
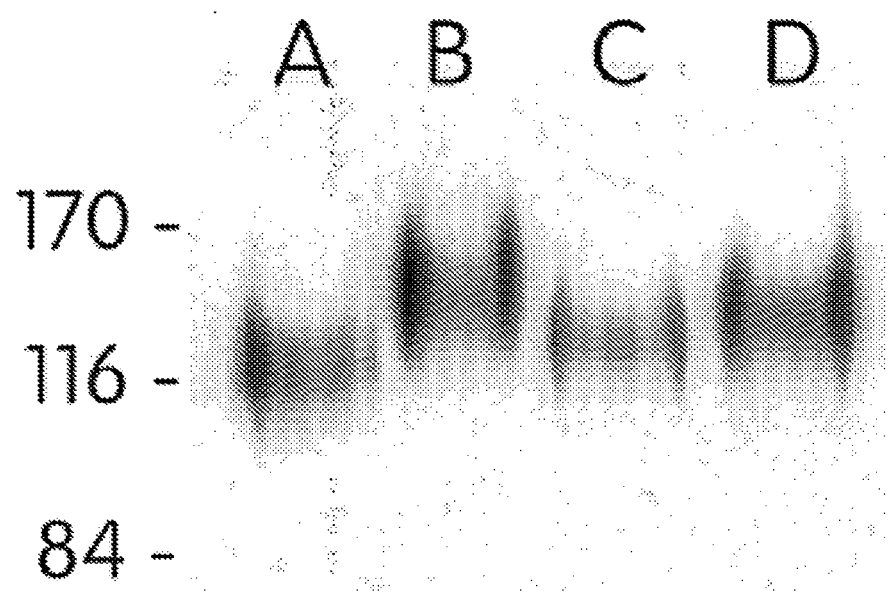
FIG. 7 is a photograph of SDA-PAGE analysis of human thymocyte and Molt-4 cell line lysate with or without sialidase treatment, followed by immunoblotting with EB-1 monoclonal antibody.

To confirm these results, SDS-PAGE and Western blotting was carried out 1 Times 10 of human thymocytes or Molt-4 tumor cells with or without sialidase treatment were suspended in 1 ml of lysis buffer solution (50 mM Tris-HCl, pH 74, 150 mM NaCl, 0.5% w/v NONIDET® P-40 and 1 mM phenylmethylsulfonyl fluoride (PMSF)), shaken at 4° C. for 30 minutes, and centrifuged at 13,000 g for 15 minutes for removal of nuclei. The supernatant were separated by electrophoresis on 10% sodium dodecyl sulfate-polyacrylamide gels (SDS-PAGE) under the reduced conditions. The acrylamide concentration of the separation gels was 10% and appropriate molecular weight markers were used. The electrophoretic transfer of proteins to nitrocellulose membranes was done at 45 V for 16 hours. After protein transfer, the nitrocellulose membranes were incubated for two hours with blocking buffer containing 5% skim milk and 0.05% TWEEN®-20 in PBS, and then incubated overnight with EB-1 antibody diluted in blocking buffer at 1 µg/ml concentration. The membranes were rinsed three times with wash buffer (PBS with 0.05% TWEEN® 20) and incubated for 1 h with affinity-purified goat anti-mouse immunoglobulin G conjugated with horseradish peroxidase diluted 1:3000 in blocking buffer. After three washes, each reactive protein band was detected by enhanced chemiluminescence (ECL) kit manufactured by Amersham Pharmacia Biotech. FIG. 7 shows a SDS-PAGE and Western blotting analysis of thyrnoeyte (A & B) and Molt-4 cell (C & D) lysate with EB-1 antibody. Lanes A and C represents the electrophoresis of cell lysate that is not treated with sialidase, whereas lanes B and D was the electrophoresis of sialidase treated lysate. EB-1 antibody recognized both sialidase-treated and untreated CD43 molecules. This suggests that EB-1 antibody might recognize unglycosylated region of CD43 molecule.

EXAMPLE 9

Figure 8:
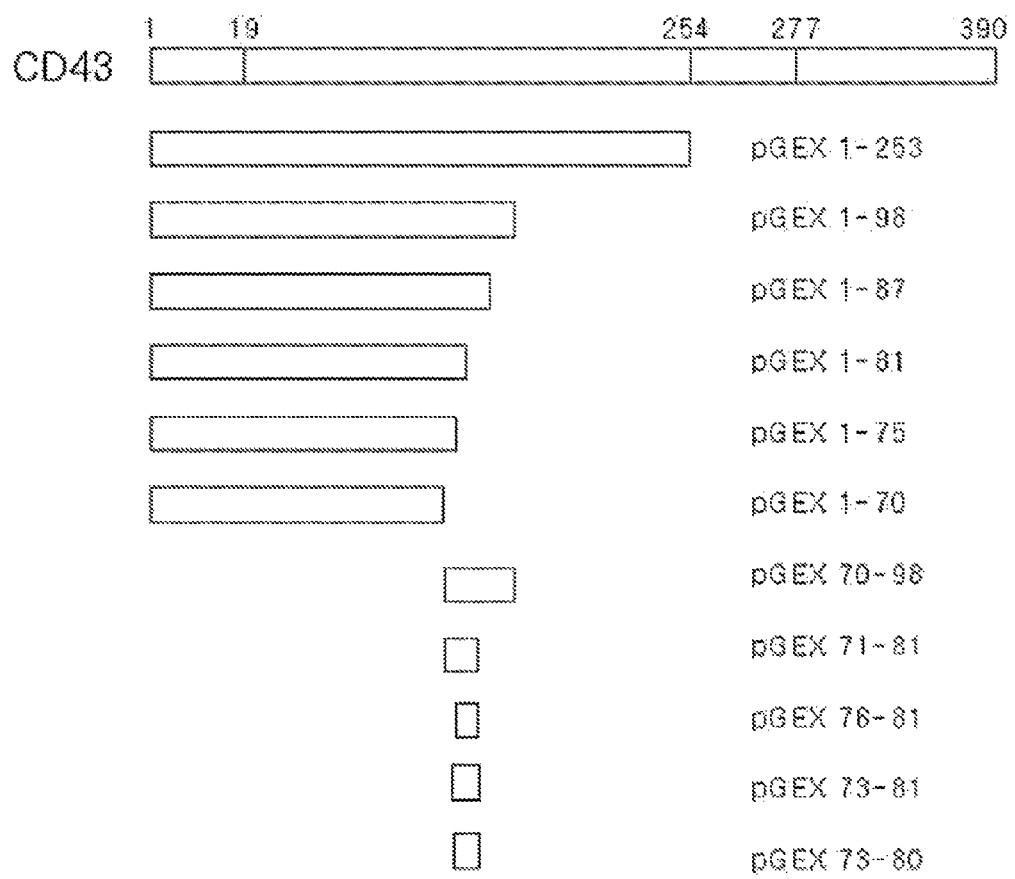
FIG. 8 is a schematic diagram of 11 types of CD43 deletion mutants.

In order to define the CD43 epitope recognized by the EB-1 antibody, CD43 mutants were constructed. The coding sequence for the human CD43 gene was amplified from a CD43 cDNA and used for the construction of expression vectors. For example, to produce glutathione-S-transferase (GST)-fusion protein, CD43 recombinant plasmids were constructed by cloning PCR fragments into pGEX-2T vector manufactured by Pharmacia. Primers used for PCR amplification were selected based on the sequence in GeneBank and modified to contain BamHI and either EcoRl, or BglII restriction sites to facilitate cloning Both purified PCR products and pGEX-2T vector were digested with BamHI and either BglII or EcoRl at 37° C. overnight, ligated using T4 DNA ligase manufactured at 16° C. overnight, and then used to transform E. coli competent TOP1OF' cells. FIG. 8 shows a schematic diagram of 11 CD43 deletion mutants. For example, the pGEX1-253 represents the pGEX-2T vector containing $1^{st}$ to $253^{rd}$ amino acids of human CD43.

To express GST-fusion proteins containing human CD43 sequences, E. coli TOP10 cells transformed with the recombinant plasmids were grown at 37° C. overnight in Luria broth (LB) medium containing 50 µg/ml ampicillin. The overnight cultured cells were diluted 20 times with fresh LB medium containing the same concentration of ampicillin and grown at 37° C. for 3 to 4 h until an optical density value of 0.6 was reached. The gene expression was induced by adding IPTG into the culture to a final concentration of 1 mM. After 4 h of incubation at 37° C. with constant shaking, the cells were pelleted by centrifugation at 6000 g for 15 minutes at 4° C. and then resuspended with 3 ml of lysis buffer (50 mM Tris-HCl, pH 8.0, 1 mM EDTA, 100 mM NaCl) for each gram of packed cells. The suspension was incubated on ice for 30 min with a final concentration of 0.2 mM PMSF.

Figure 9:
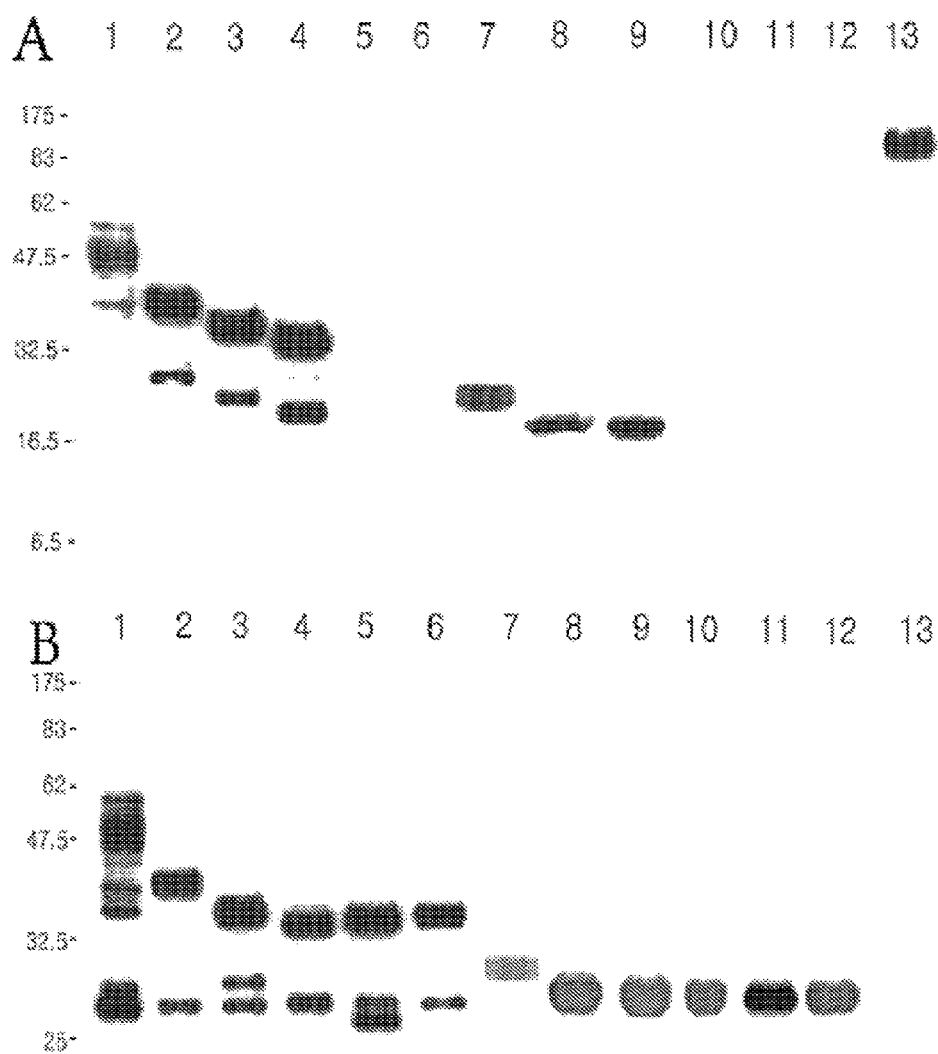
FIG. 9 is a photograph of SDA-PAGE analysis of 11 types of CD43 deletion mutants, followed by immunoblotting with EB-1 monoclonal antibody and anti-GST polyclonal antibody.

For Western blotting of CD43 mutants with EB-1 antibody, aliquots of each lysate of GST-CD43 fusion protein were separated by electrophoresis on 10% sodium dodecyl sulfate (SDS)-polyacrylamide gels followed by blotting onto nitrocellulose membranes. The nitrocellulose membrane was stained with EB-1 antibody or anti-GST polyclonal antibody and each reactive protein band was detected by enhanced chemiluminescence according to the procedure of Example 8. FIG. 9 shows the Western blotting analysis of CD43 mutant with EB-1 (A) and anti-GST (B) antibodies. Lane 1 represent pGEX1-253, lane 2 pGEXI-98, lane 3 pGEX1-87, lane 4 pGEX1-81, lane 5 pGEXI-75, lane 6 pGEXI-70, lane 7 pGEX70-99, lane 8 pGEX71-81, lane 9 pGEX73-81, lane 10 pGEX76-81, lane 11 pGEX73-80, lane 12 pGEX2T, and lane 13 human thymocyte lysate. As shown in FIG. 9, pGEX73-81 contains the minimal sequence for recognition of CD43 antigen by EB-1 and thus CD43 epitope for EB-1 antibody is $73^{rd}$ to $81^{st}$ amino acid sequence of CD43. The sequence is as follows, Glu Gly Ser Pro Leu Trp Thr Ser Ile (SEQ ID NO: 2). Therefore, this sequence is very useful in the aspect that the epitope recognized by EB-1 antibody is not expressed on mature blood cell, hematopoietic stem cells, subsets of hematopoietic precursors in bone marrow or any non-hematopoietic tissues.

EXAMPLE 10

Figure 10:
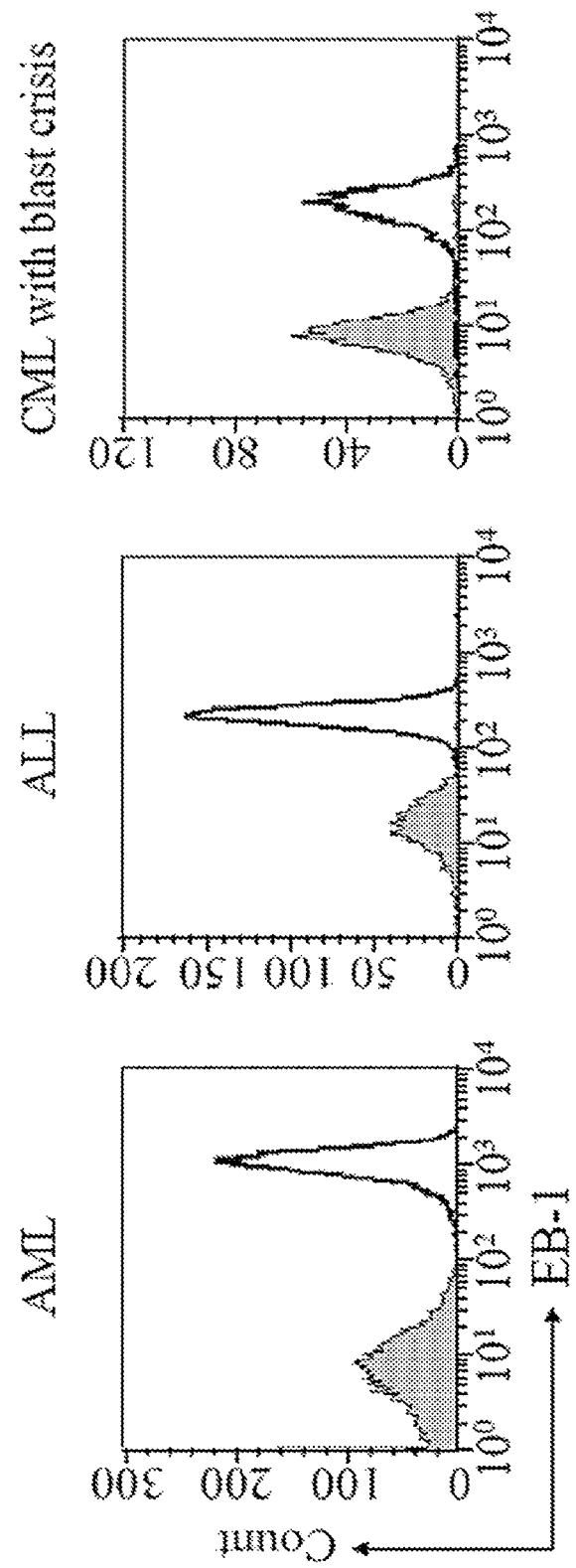
FIG. 10 is a photograph of the reactivity of EB-1 monoclonal antibody on the surface of human leukemic cells using single color flow cytometry.

Example 3, 5, 6 and 7 show that EB-1 immunoreactivity is restricted to subsets of hematopoietic precursors in bone marrow except for hematopoietic stem cells. In this example the expression of CD43 epitope recognized by EB-1 antibody on leukemic cells were investigated according to flow cytometric analysis of Example 3. Peripheral blood was collected in EDTA tube from leukemia patients and erythrocytes and mature granulocyte were removed by centrifugation using Ficoll-Hypaque manufactured Amersham Pharmacia Biotech. The purified cells were stained with FITC-conjugated EB-1 and analyzed using flow cytometer. Table 4 below is the results of marker analysis of leukemic samples using EB-1 antibody by flow cytometry. In 31 of 38 leukemia cases (81.6%), which include acute myelogenous leukemia (AML), acute lymphogenous leukemia (ALL) and chronic myelogenous leukemia (CML) with blast crisis, tumor cells are stained by EB-1 antibody. FIG. 10 shows the representative flow cytometric staining pattern of leukemic cells using EB-1 antibody. The solid line represents the staining by EB-1 antibody, and the negative staining profile by an irrelevant antibody is shown as filled histogram.

TABLE 4

| Type of leukemia | EB-1 positivity | | |
|---|---|---|---|
| | No. of cases | No. of cases | % |
| AML | 22 | 20 | 90.9 |
| M1 | 6 | 6 | 100.0 |
| M2 | 8 | 7 | 87.5 |
| M3 | 1 | 1 | 100.0 |
| M4 | 4 | 4 | 100.0 |
| Others | 3 | 2 | 66.7 |
| ALL | 13 | 9 | 69.2 |
| CML with blast crisis | 3 | 2 | 66.7 |
| Total | 38 | 31 | 81.6 |

Figure 11:
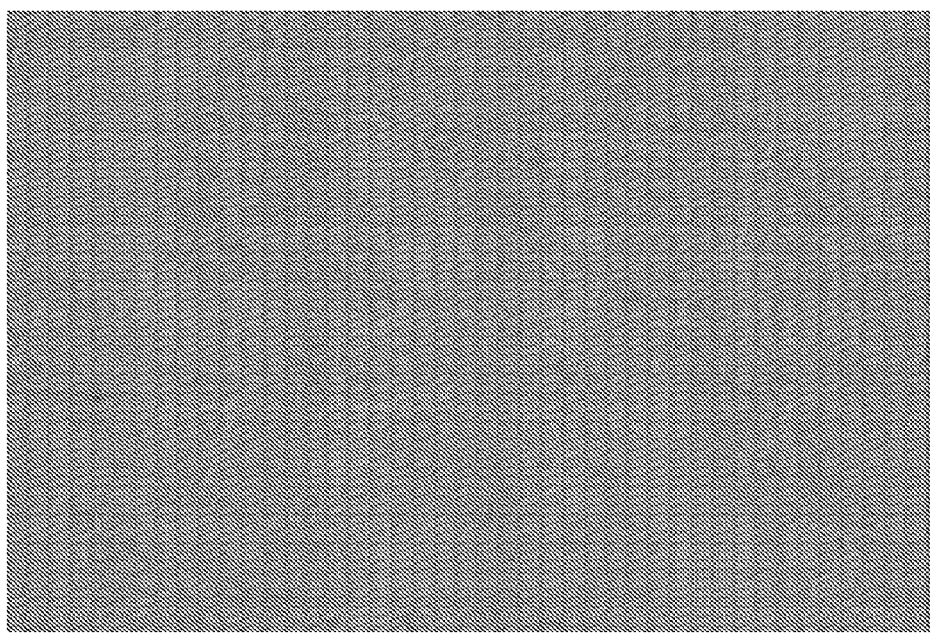
FIG. 11 is a photograph of immunohistochemical staining of lymphoblastic lymphoma tissue by EB-1 monoclonal antibody.

The present example was also carried out according to immunohistochemical analysis of Example 2 to investigate whether EB-1 antibody is reactive against lymphoblastic lymphoma cells using EB-1 antibody purified from Example 4 as primary antibody. FIG. 11 shows the representative immunostaining pattern of lymphoblastic lymphoma tissue by EB-1 antibody. As a whole, 4 out of 9 (44.4%) lymphoblastic lymphoma cases showed positive staining by EB-1 antibody. Therefore, EB-1 antibody and its CD43 epitope could be powerful diagnostic and therapeutic tools for various types of acute leukemia, chronic leukemia with blast crisis and lymphoblastic lymphoma

EXAMPLE 11

Figure 12:
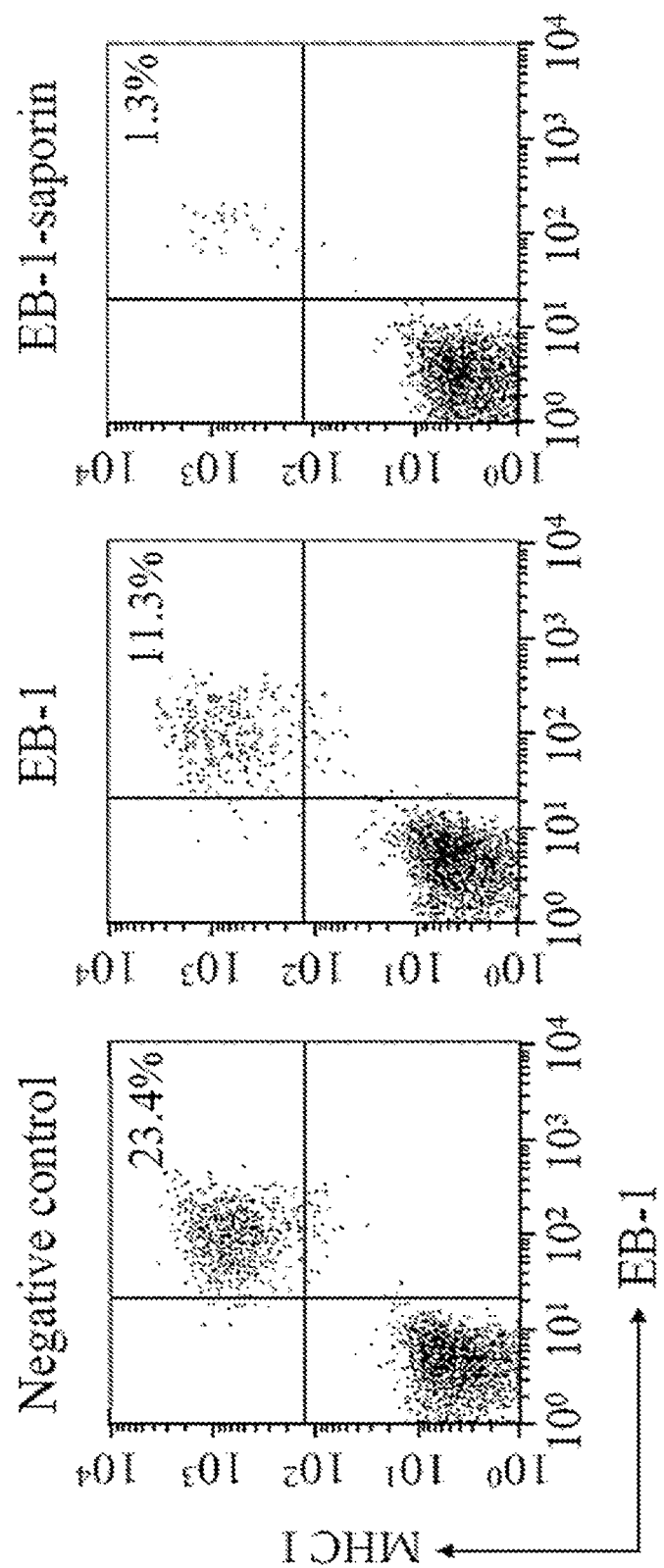
FIG. 12 is a photograph of the reactivity of EB-1 and anti-human MHC class I monoclonal antibodies using dual color flow cytometry on the surface of leukemic cells in the peripheral blood of RAG-1-deficient mice in which CCRF-CEM cells were intravenously injected and treated with EB-1 or control antibody.

In order to determine the therapeutic potential of EB-1 antibody, EB-1 immunotoxin and human leukemia model in mice were developed. To produce immunotoxin, saporin manufactured by Sigma, and EB-1 antibody were conjugated via a disulfide bond between chemically inserted sulfhydryl (SH) groups (Polito et al., 2004). The human leukemia model in mice was established by the injection of 2×105 CCRF-CEM cells in a 300 µl volume of PBS into the tail vein of RAG-1-deficient mice. One week later, each mouse was treated with four 100 pg doses of either of EB-1 antibody, EB-1-saporin immunotoxin, or irrelevant antibody as a bolus injection (in a 300 µl volume of PBS) into the tail vein in every other day (i.e. days 7, 9, 11 and 13). Four weeks after intravenous injection of CCRF-CEM cells, blood sample from the retro-orbital plexus was stained with FITC-conjugated EB-1 antibody and PE-conjugated anti-human MHC class I antibody according to flow cytometric analysis of Example 3 and 10. FIG. 12 is representative result of flow cytometric analysis of leukemic cells in blood from the mice. In control mice, 23.4% of cells in peripheral blood was both human (CD43- and human MHC class I-positive CCRF-CEM cells, where CCRF-CEM cells was reduced up to 1.3% in the mouse treated with EB-1-saporin immunotoxin. The leukemic cell burden was also decreased about two-fold in the mouse treated with EB-1 antibody only, compared with that in control mouse. Thus, EB-1 antibody could provide effective tools for treatment of acute leukemic cells through the delivery of toxic material into the tumor cells, antibody-dependent cell mediated cytotoxicity (ADCC), or other mechanisms.

EXAMPLE 12

Figure 13:
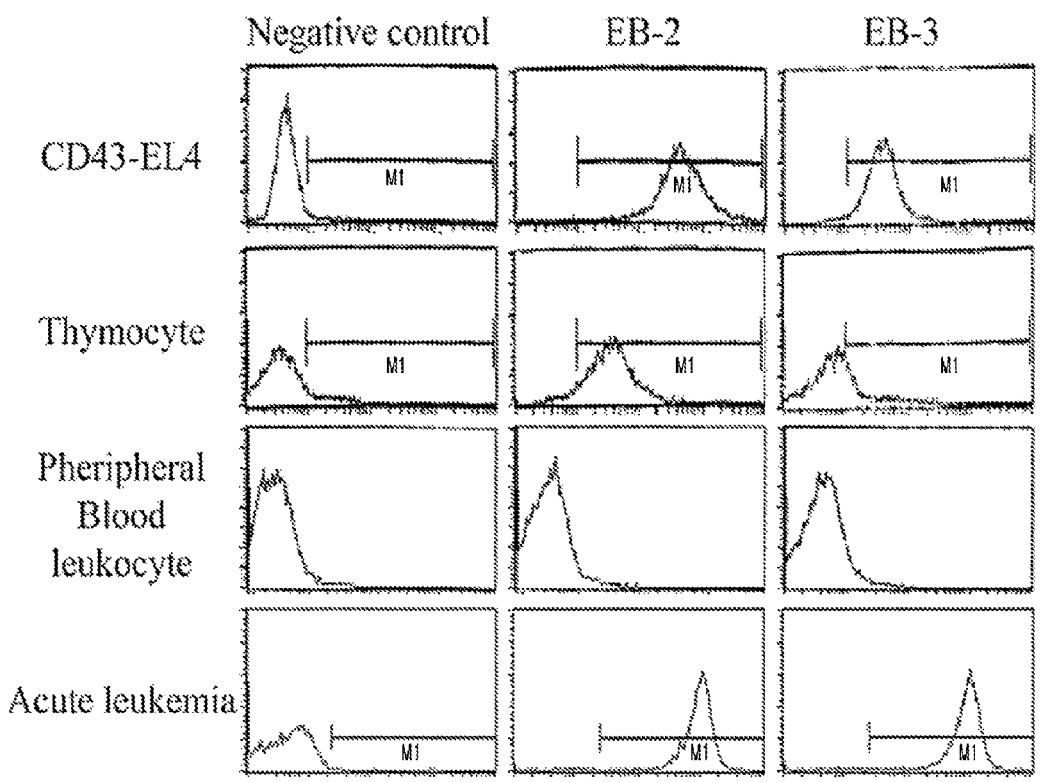
FIG. 13 is a photograph of the reactivity of two additional anti-CD43 antibodies (EB-2 and EB-3), which were produced by immunization of mice with CD43 epitope, on the surface of CD43-transfected ETA cell line, human thymocytes, human peripheral blood leukocytes, and human leukemia sample using single color flow cytometry.

EB-1 antibody recognizes the $73^{rd}$ to $81^{st}$ amino acid sequence of CD43, Glu Gly Ser Pro Leu Trp Thr Ser Ile (SEQ ID NO: 2). The present example was carried to develop new anti-CD43 antibodies that are useful for the diagnosis and treatment of leukemia and lymphoma. DNA fragment encoding $70^{th}$ to $98^{th}$ amino acid sequence of CD43 that include SEQ ID NO:2 were cloned into pQE-40 vector, and then used to transform competent E. coli TOP10F' cells. Transformed TOP10F' cells were cultured according the methods of Example 9, and CD43 fusion protein was purified from the E. coli lysate by the passing of E. coli lysate through Nickel column manufactured by Amersham Pharmacia Biotech. 100 µg of SY-CD43 fusion protein was mixed with complete Freund's adjuvant and intraperitoneally administered and immunized into the Balb/c mice. Four weeks later, additional two 100 µg doses of SY-CD43 fusion protein mixed with incomplete Freund's adjuvant at two weeks interval intraperitoneally administered. Three days after final boosting, the spleen was removed from the immunized mice and hybridoma cells were prepared according the fusion method of Example 1. The culture supernatant of hybridoma cells was screened using human CD43-transfected murine EL4 cells by flow cytometry, and two hybridoma clones that are reactive against CD43-transfected EL4 cells were selected and named as EB-2 and EB-3, respectively. FIG. 13 shows the flow cytometric analysis of CD43-transfected EL4 cell line, human thymocyte, human peripheral blood cells, and human acute leukemia cells by EB-2 and EB-3 antibodies. CD43-transfected EL4 cell line, human thyrnoeytes and human leukemic cells were positive, but human peripheral blood cells were negative to both EB-2 and EB-3 antibodies. Thus, staining pattern of both EB-2 and EB-3 antibodies is similar to that of EB-1.

EXAMPLE 13

Figure 14:
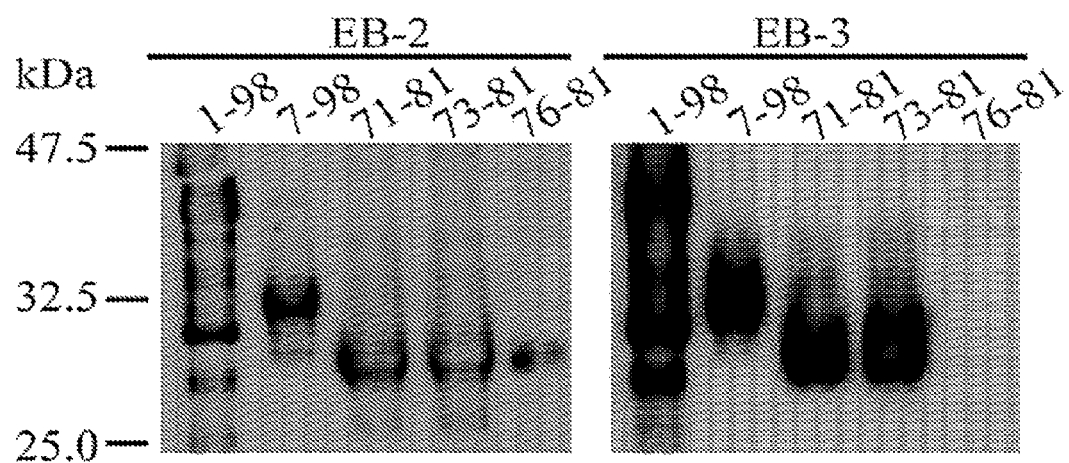
FIG. 14 is a photograph of SDA-PAGE analysis of 5 types of CD43 deletion mutants, followed by immunoblotting with EB-2 and EB-3 monoclonal antibodies.

The present example was carried out to determine the CD43 epitope recognized by EB-2 and EB-3 antibodies according the SDS-PAGE and Western blotting of Example 9 using CD43 deletion mutants. FIG. 14 shows the Western blotting analysis of CD43 mutant with EB-2 and EB-3. The CD43 epitope for EB-3 antibodies is similar to that for E δ 1. That is, the minimal epitope for both EB-1 and EB-3 antibodies are $73^{rd}$ to $81^{st}$ amino acid sequence of CD43 (SEQ ID NO: 2; Glu Gly Ser Pro Leu Trp Thr Ser Ile). However, EB-2 antibody could recognize the smaller peptide sequence than EB-1 and EB-3. The minimal epitope for EB-2 is $76^{th}$ to $81^{st}$ amino acid sequence of CD43. The sequences is as follows, Pro Leu Trp Thr Ser Ile (SEQ ID NO: 1).

The CD43 epitope of the present invention is useful for the diagnosis of acute leukemia, chronic leukemia with blast crisis, and lymphoblastic lymphoma by determination whether this CD43 epitope is expressed upon tissue examination or peripheral blood examination because this the CD43 epitope of the present invention is not found in normal non-hematopoietic tissue, mature blood cells, and activated peripheral blood except thymocytes. The CD43 epitope of the present invention can be used as target material for the treatment of acute leukemia, chronic leukemia with blast crisis, and lymphoblastic lymphoma because it is not expressed on hematopoietic stem cells and normal tissue except thymocytes and subsets of hematopoietic precursors in bone marrow.

The description of exemplary embodiments of biologically active polypeptides is illustrative of the present invention. Because of the variation which will be apparent to those skilled in the art, however, the present invention is not intended to be limited to the particular embodiments described above. The scope of the invention is defined in the following claims.

What is claimed is:

1. A method of treating a tumor of a subject, wherein the tumor is selected from the group consisting of leukemia, chronic leukemia with blast crisis and lymphoblastic lymphoma, comprising administering to the subject a therapeutically effective amount of a monoclonal antibody, or an antigen-binding fragment thereof, which specifically binds to a polypeptide of CD43, wherein the polypeptide consists of the amino acid sequence of SEQ ID NO:1 or 2.

2. The method of claim 1, wherein the monoclonal antibody or an antigen-binding fragment thereof specifically binds to an epitope of CD43 consisting of an amino acid sequence of SEQ ID NO: 1 or SEQ ID NO: 2.

3. The method of claim 1, wherein the monoclonal antibody or antigen binding fragment is in purified form, and wherein the antibody is not an antibody produced by the hybridoma deposited as KCLRF-BP-00010.

4. The method of claim 1, wherein the monoclonal antibody or antigen binding fragment is linked to a toxic material selected from the group consisting of radioisotopes, toxic chemicals, toxic proteins and anti-tumor agents.

5. The method of claim 1, wherein the monoclonal antibody is a chimeric or humanized monoclonal antibody.

6. The method of claim 1, wherein the monoclonal antibody is a human monoclonal antibody.

* * * * *

SEQUENCE LISTING

<160> NUMBER OF SEQ ID NOS: 2

<210> SEQ ID NO 1
<211> LENGTH: 6
<212> TYPE: PRT
<213> ORGANISM: human

<400> SEQUENCE: 1

Pro Leu Trp Thr Ser Ile
1               5

<210> SEQ ID NO 2
<211> LENGTH: 9
<212> TYPE: PRT
<213> ORGANISM: human

<400> SEQUENCE: 2

Glu Gly Ser Pro Leu Trp Thr Ser Ile
1               5